United States Patent
Osawa et al.

(10) Patent No.: US 7,138,429 B2
(45) Date of Patent: Nov. 21, 2006

(54) FLAVONOID COMPOUND AND PROCESS FOR PRODUCING THE SAME

(75) Inventors: Toshihiko Osawa, Nagoya (JP); Kenichiro Minato, Sendai (JP); Yoshiaki Miyake, Toyota (JP)

(73) Assignee: Japan Sci. Tech. Corp., Saitama (JP)

( * ) Notice: Subject to any disclaimer, the term of this patent is extended or adjusted under 35 U.S.C. 154(b) by 305 days.

(21) Appl. No.: 10/471,438

(22) PCT Filed: Mar. 14, 2002

(86) PCT No.: PCT/JP02/02445

§ 371 (c)(1),
(2), (4) Date: Sep. 10, 2003

(87) PCT Pub. No.: WO02/074971

PCT Pub. Date: Sep. 26, 2002

(65) Prior Publication Data

US 2004/0152762 A1    Aug. 5, 2004

(30) Foreign Application Priority Data

Mar. 15, 2001  (JP) ............................ 2001-073577
Mar. 30, 2001  (JP) ............................ 2001-098744

(51) Int. Cl.
*A61K 31/352* (2006.01)
*C07D 311/74* (2006.01)

(52) U.S. Cl. ................... 514/456; 549/356; 549/381; 549/399; 549/401; 514/451

(58) Field of Classification Search ............... 549/200, 549/356, 381, 396, 399, 401; 514/451, 458
See application file for complete search history.

(56) References Cited

U.S. PATENT DOCUMENTS 6,133,241 A    10/2000    Bok et al.

OTHER PUBLICATIONS

Braca et al (1999): STN International CAPLUS database, Columbus (Ohio), accession No. 1999: 512181.*
Bilia et al (1996): STN International CAPLUS database, columbus (Ohio), accession No. 1997: 192736.*
European Patent Office, Communication re: Application No. 027 052 08.3-2402-JP020 244 45 (Feb. 13, 2004) (EPO Search Report).
Basudeb Achari et al., Two Isomeric Flavones From Vitex Negundo 23 Phytochemistry 703 (1984).
Peter Proksch et al., New Dihydroflavonols from Enceliopsis and Geraea, 1987 Planta Medica 334 (1987).
S. Shandra et al., Synthesis of 5,4'-dihydroxy-7,8,3-40 ,5'-tetramehoxyflavone & Two New Isomeric Pentaoxygenated . . . , 26B Indian J. Chemistry 82 (1987).
Minato Kenishiro, Lemon-Fermented Product and Method for Producing Same, Japan Patent Office Publication No. 2002355004 (Dec. 10, 2002) (Abstract machine-translated into English, and full publication in Japanese).
Fukumoto Shuichi, Fermented Lemon and Method for Producing the Same, Japan Patent Office Publication No. 2003102429 (Apr. 8, 2003) (Abstract machine-translated into English, and full publication in Japanese).
Fukumoto Shuichi, Fermented Citrus and Method for Producing the Same, Japan Patent Office Publication No. 2003102430 (Apr. 8, 2003) (Abstract machine-translated into English, and full publication in Japanese).

* cited by examiner

*Primary Examiner*—Golam M. M. Shameem
(74) *Attorney, Agent, or Firm*—Pharmaceutical Patent Attorneys, LLC

(57) ABSTRACT

A preparation process is provided for preparing a novel flavonoid compound having a high level of antioxidative action. The flavonoid compound is obtained by subjecting hesperidin to microbial fermentation treatment with *Aspergillus saitoi*.

8 Claims, 1 Drawing Sheet

FLAVONOID COMPOUND AND PROCESS FOR PRODUCING THE SAME

BACKGROUND OF THE INVENTION

The present invention relates to a novel flavonoid compound and a process for preparing the same.

Hesperidin, conventionally known as vitamin P, is a glycoside of hesperetin, and a flavonoid compound that is contained in large amounts in oranges, lemons and other citrus fruits, and particularly in the rind of unripe fruit. Hesperidin is found in abundance in nature, and even though it possesses physiological activity such as antiallergic action, antiviral action and capillary reinforcing action, the range of its utilization has been limited. For example, since it is difficult for hesperidin to be absorbed by the body, the resulting antioxidative effects are extremely low, thereby preventing it from being used as an antioxidant. It is therefore expected that hesperidin will be used more effectively in the future.

BRIEF SUMMARY OF THE INVENTION

An object of the present invention is the effective utilization of hesperidin in various fields. Another object of the present invention is to provide a novel flavonoid compound that possesses comparatively high antioxidative action, and a process for preparing the compound.

In order to achieve the above objects, in one aspect of the present invention, a flavonoid compound is provided that has a structure represented by the following chemical formula.

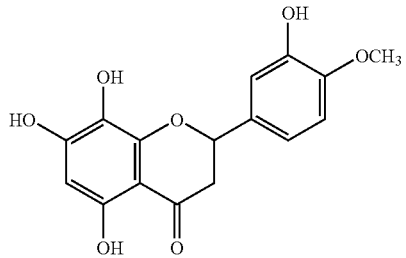

This flavonoid compound is characterized in that it has antioxidative action.

The flavonoid compound is also characterized in that it is obtained by microbial fermentation treatment of hesperidin using *Aspergillus saitoi*.

In another aspect of the present invention, a process for preparing a flavonoid compound is provided. The process is characterized in that it comprises a step of subjecting hesperidin to microbial fermentation with *Aspergillus saitoi* to form a flavonoid compound by microbial conversion of hesperidin.

The microbial fermentation step is characterized in that it comprises a step of culturing mycelia wherein a medium containing hesperidin and *Aspergillus saitoi* is shake cultured to convert hesperidin to hesperetin in the vegetative mycelia of *Aspergillus saitoi*, and a step of forming spore wherein a flavonoid compound is microbially converted from the hesperetin in the medium while promoting spore formation from the vegetative mycelia.

The spore formation step may be carried out while continuing shake culturing or after switching to stationary culturing. However, in the case of stationary culturing, it is preferred that the depth of the medium be reduced, the ratio of surface area to culture volume (specific surface area) increased, and aerobic conditions maintained throughout the medium in order to increase the microbial conversion rate by *Aspergillus saitoi*.

A pre-culturing step is preferably carried out in which a medium containing *Aspergillus saitoi* is shake cultured prior to the mycelia culturing step.

DETAILED DESCRIPTION OF THE PREFERRED EMBODIMENTS

Figure 1:
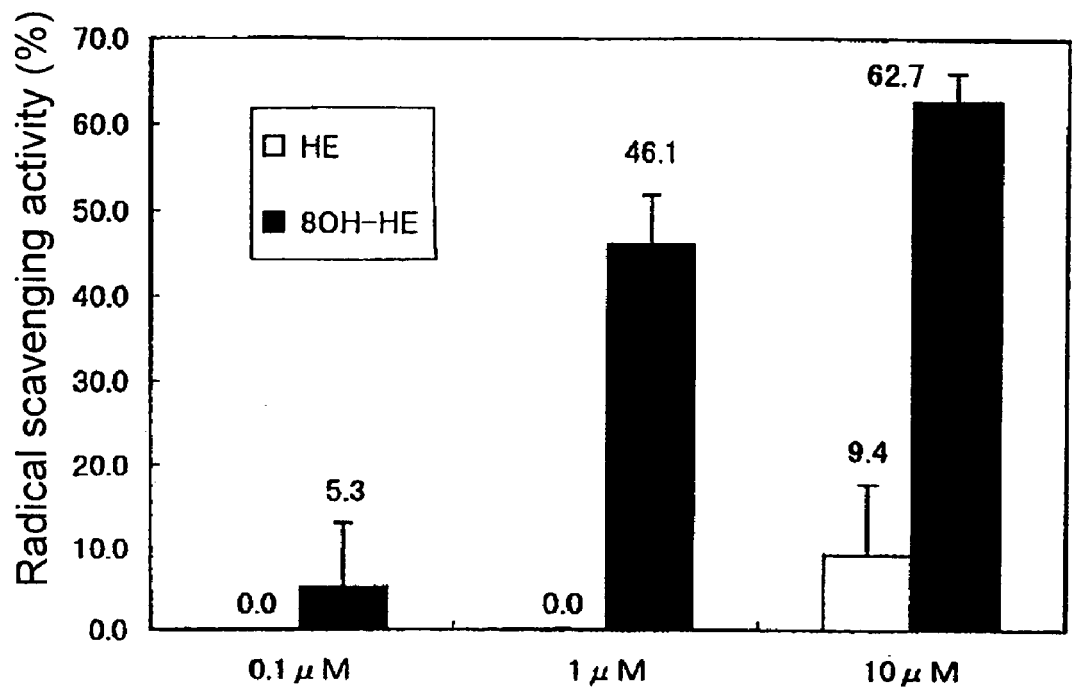
FIGS. 1 and 2 are graphs showing the results of measuring the antioxidative activity of flavonoid compounds.

The following provides a detailed explanation of a flavonoid compound and its preparation process in accordance with one embodiment of the present invention.

The flavonoid compound of one embodiment of the present invention has a structure represented by chemical formula 1.

(Chemical Formula 1)

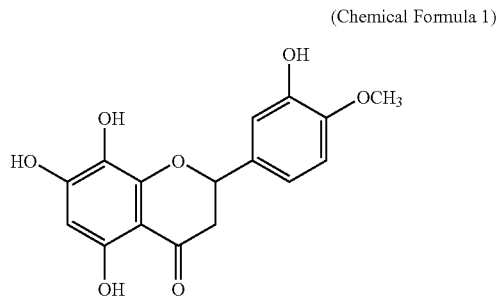

The composition formula of the flavonoid compound is $C_{16}H_{14}O_7$, its molecular weight is 318.27, and its name is 3',5,7,8-tetrahydroxy-4'-methoxyflavonone or 2,3-dihydro-5,7,8-trihydroxy-2-(3-hydroxy-4-methoxyphenyl)-4H-1-benzopyran-4-one. As is represented by the chemical formula, the flavonoid compound is an organic compound having a hydroxyl group at the 8-position of hesperetin (3',5,7-trihydroxy-4'-methoxyflavonone; $C_{16}H_{14}O_6$), and is referred to as so-called 8-hydroxyhesperetin.

8-Hydroxyhesperetin easily dissolves in methanol, ethanol and dimethyl sulfoxide (DMSO), and is also somewhat soluble in water. In contrast to hesperetin which hardly exhibits any antioxidative action, 8-hydroxyhesperetin exhibits an extremely high level of antioxidative action comparable to that of α-tocopherol (vitamin E). In the case of adding 8-hydroxyhesperetin to, for example, foods or beverages, health foods and health drinks (having compositions that contain 8-hydroxyhesperetin) can be produced that have health promoting activity due to the antioxidative action of 8-hydroxyhesperetin. Ingested 8-hydroxyhesperetin removes active oxygen in the living body and inhibits the formation of lipid peroxides, making it effective in preventing lifestyle-related diseases such as cancer, arteriosclerosis, diabetes and their complications caused by oxidative stress.

8-Hydroxyhesperetin is obtainable by microbial fermentation treatment of hesperidin with *Aspergillus saitoi*. More specifically, 8-hydroxyhesperetin is prepared in the method described below. First, *Aspergillus saitoi* is cultured in a medium containing hesperidin (vitamin P), a glycoside formed with hesperetin and rutinose (L-rhamnosyl-D-glucose) The cultured *Aspergillus saitoi* forms 8-hydroxyhesperetin from hesperidin by microbial conversion. The 8-hydroxyhesperetin is contained in the supernatant of the culture liquid. *Aspergillus saitoi* is preferably cultured at a culturing temperature of 20 to 40° C. under aerobic conditions to ensure satisfactory growth and microbial conversion by *Aspergillus saitoi*.

Preferable examples of media include mold media such as potato dextrose-containing medium and Czapek's medium, or various liquid media containing an organic substance such as bean curd refuse. Minimal medium containing the minimum required nutrients is preferably used in order to inhibit fermentation other than fermentation for converting from hesperidin to 8-hydroxyhesperetin. For example, media that is free of monosaccharides and disaccharides is preferable so as to inhibit alcohol fermentation. The pH of the medium at the start of culturing is preferably within the range of 3 to 7 to facilitate the growth of *Aspergillus saitoi*.

A comparatively low concentration of an organic solvent is preferably added to the medium to enhance the solubility of hesperidin in the medium. Examples of organic solvents include methanol, ethanol and DMSO. DMSO is used most preferably since hesperidin dissolves comparatively easily in this solvent. The concentration (content) of DMSO in the medium is preferably 0.01 to 5% by volume, and more preferably 0.01 to 1% by volume. In the case where the concentration of DMSO in the medium is less than 0.01% by volume, an adequate amount of hesperidin is not dissolved in the medium, while in the case where the concentration of DMSO exceeds 5% by volume, the growth of *Aspergillus saitoi* is remarkably inhibited. The organic solvent may be added to the medium simultaneous to the addition of hesperidin, or may be added to the medium prior to the addition of hesperidin.

The hesperidin is preferably added to the medium at as high a concentration as possible to efficiently obtain 8-hydroxyhesperetin. In other words, it is preferable that the content of hesperidin in the medium be the saturation concentration (solubility limit) of the hesperidin with respect to the medium. Although the saturation concentration of hesperidin varies according to the amount of organic solvent added to the medium, it is roughly 0.3% by weight or less.

*Aspergillus saitoi* is preferably added to the medium at a concentration of at least $2 \times 10^6$ cfu/ml at the start of culturing to efficiently obtain 8-hydroxyhesperetin in a short period of time.

In order to improve the efficiency of the microbial conversion by *Aspergillus saitoi*, vegetative mycelia of *Aspergillus saitoi* are shake cultured in a medium (mycelia culturing step). Subsequently, the vegetative mycelia are preferably allowed to form spores.

In order to allow adequate formation of vegetative mycelia, prior to the mycelia culturing step, a medium containing mold only (*Aspergillus saitoi*) preferably preliminarily shake cultured (pre-culturing step). In the case of carrying out a pre-culturing step, the microbial conversion efficiency of hesperidin improves since growth inhibition of *Aspergillus saitoi* in the initial culturing stage (early growth phase) by an organic solvent is avoided. The pre-culturing step is preferably carried out until vegetative mycelia of *Aspergillus saitoi* cover about one-half of the surface of the culture liquid.

In the mycelia culturing step, *Aspergillus saitoi* is shake cultured in a medium containing hesperidin. As a result of shake culturing, the vegetative mycelia of *Aspergillus saitoi* are able to carry out microbial conversion under aerobic conditions. More specifically, in the mycelia culturing step, a glycosidase reaction is efficiently carried out in which the vegetative mycelia form hesperetin by severing the bonds between hesperetin and rutinose within hesperidin. The shaking rate during shake culturing is preferably within the range of 50 to 200 rpm/minute. In the case where the shaking rate is less than 50 rpm/minute, mycelia growth is inadequate since the entire medium that contains the *Aspergillus saitoi* is not kept sufficiently aerobic. Conversely, in the case where the shaking rate exceeds 200 rpm/minute, mycelia are not adequately formed due to violent shaking of the medium.

The amount of hesperidin added to the medium may exceed the previously mentioned solubility limit. Hesperidin that has been added in excess of the solubility limit does not dissolve in the medium at the time of its addition. However, the hesperidin is suitably dissolved in the medium and is utilized for microbial fermentation due to the agitating action generated by shaking. In this case, it is preferable to shake at about 50 rpm/minute until the hesperidin is no longer visible to make it difficult for the hesperidin to precipitate on the bottom of the culture container. As a result, more hesperidin is produced.

The spore formation step is carried out after an adequate amount of hesperetin has been formed in the medium. In the spore formation step, *Aspergillus saitoi* is stationary or shake cultured without replacing the medium after the mycelia culturing step. As a result of this spore formation step, vegetative mycelia of *Aspergillus saitoi* carry out microbial conversion while forming spores.

At completion of the mycelia culturing step, vegetative mycelia of *Aspergillus saitoi* are densely present on the surface of the culture (liquid surface). These mycelia can be confirmed visually. Therefore, the timing for transition from the mycelia culturing step to the spore formation step is determined by using the density of vegetative mycelia on the surface of the culture as an indicator.

In the spore formation step, vegetative mycelia of Aspergillus saitoi carry out a hydroxylase reaction in which a hydroxyl group is added to the 8-position of hesperetin while being allowed to form spores. Thus, 8-hydroxyhesperetin is formed extremely efficiently. The formation reaction of 8-hydroxyhesperetin is carried out most efficiently from the intermediate stage to the latter stage of the spore formation step within the culture container. On the other hand, at the stage where spore formation has been completed, the formation efficiency is comparatively low. Consequently, in order to efficiently obtain 8-hydroxyhesperetin in a short period of time, culturing is preferably interrupted immediately before the entire surface of the culture container is completely covered with spores followed by extraction of the formed 8-hydroxyhesperetin.

In the case of carrying out stationary culturing in the spore formation step, the inhibition of spore formation due to physical irritation attributable to shaking can be avoided. It should be noted that during stationary culturing, it is preferable to prepare a comparatively thin (shallow) medium using a container having a large bottom surface in order to increase the ratio of surface area to volume of the medium (specific surface area). Since the use of comparatively thin medium allows the maintaining of aerobic conditions throughout the medium, the activity of *Aspergillus saitoi* is enhanced and the efficiency of microbial conversion is improved.

On the other hand, in the case of carrying out shake culturing in the spore formation step, since aerobic conditions are maintained easily irregardless of the specific surface area of the medium, a comparatively large amount of 8-hydroxyhesperetin can be obtained in a single culturing procedure.

The 8-hydroxyhesperetin is purified after being extracted from the culture supernatant or from the medium following the spore formation step. For example, a supernatant fraction is obtained by centrifugal separation of the medium at a speed to such a degree that does not cause the cell membrane of *Aspergillus saitoi* to be ruptured (about 3000 rpm). The supernatant fraction is purified by reverse phase liquid chromatography using an octadecyl group chemically bonded silica (ODS) column.

Since a comparatively large amount of 8-hydroxyhesperetin is also contained in the precipitated fraction following centrifugal separation, 8-hydroxyhesperetin may also be extracted from the precipitated fraction. For example, an organic solvent such as methanol or ethanol is added to the precipitated fraction, and while adequately washing the precipitated fraction, 8-hydroxyhesperetin is extracted into the organic solvent. Purified 8-hydroxyhesperetin is then obtained from the extract by reverse phase liquid chromatography.

The following advantages are obtained according to one embodiment of the present invention.

The flavonoid compound, namely 8-hydroxyhesperetin of one embodiment of the present invention has a novel structure that has a hydroxyl group added to the 8-position of hesperetin. 8-Hydroxyhesperetin demonstrates remarkably high antioxidative action as compared with hesperidin and hesperetin. Consequently, since it inhibits the formation of lipid peroxides by removing active oxygen in the body, it is useful in preventing lifestyle-related diseases such as cancer, arteriosclerosis, diabetes and their complications caused by oxidative stress.

The flavonoid compound (8-hydroxyhesperetin) according to one embodiment of the present invention is prepared from hesperidin by microbial fermentation treatment using *Aspergillus saitoi*. More specifically, hesperidin is microbially converted to a flavonoid compound having enhanced antioxidative activity by *Aspergillus saitoi*. Thus, the production of 8-hydroxyhesperetin is comparatively easy.

The raw material of the flavonoid compound (8-hydroxyhesperetin) of one embodiment of the present invention is a natural ingredient contained in citrus fruits, namely hesperidin. Hesperidin is subjected to microbial treatment by *Aspergillus saitoi*, which is used in the brewing of alcoholic beverages such as distilled spirits. Thus, the flavonoid compound may be ingested by humans without raising any problems.

The novel flavonoid compound (8-hydroxyhesperetin) is produced by microbial fermentation treatment of hesperidin by *Aspergillus saitoi*. Thus, the range of utilization of hesperidin is expanded by the preparation process of a flavonoid compound according to one embodiment of the present invention.

According to the preparation process of a flavonoid compound of one embodiment of the present invention, novel flavonoid compounds can be produced extremely easily using microorganisms.

According to the preparation process of one embodiment of the present invention, a spore formation step is carried out after shake culturing of medium containing hesperidin and *Aspergillus saitoi*. Thus, 8-hydroxyhesperetin is produced extremely efficiently using an extremely simple procedure.

In the case of carrying out a pre-culturing step prior to the mycelia culturing step, the efficiency of microbial conversion of hesperidin is improved since inhibition of the growth of *Aspergillus saitoi* in the initial stage of culturing can be avoided.

EXAMPLES

The following provides an explanation of examples and comparative examples that embody the embodiments of the present invention described above.

<Hesperidin Conversion Product Preparation Process>

A suspension of *Aspergillus saitoi* spores was prepared to a spore concentration of at least $2 \times 10^8$ spores/ml using an *Aspergillus saitoi* strain (IAM No. 2210) subcultured from the Institute of Applied Microbiology (IAM). 100 ml aliquots of potato dextrose broth medium (Difco) were placed in several Erlenmeyer flasks (volume: 500 ml). The medium was sterilized by keeping the flasks at 121° C. for 15 minutes in an autoclave. After cooling, 1.0 ml aliquots of the spore suspension were added to each flask to inoculate the medium. Vegetative mycelia were then grown by shake culturing at 100 rpm/minute in a constant temperature chamber (having the same aerobic conditions as air) at 30° C.

The vegetative mycelia were adequately grown by continuing shake culturing over the course of 10 days. 10% by weight of hesperidin diluent was prepared by dissolving hesperidin (Sigma) in DMSO, followed by sterilization in an autoclave (105° C., 5 minutes). 5 ml aliquots of the hesperidin solution were added to each flask. Shake culturing was continued under the same aerobic conditions to allow the formation of spores from the vegetative mycelia. As a result of monitoring the status of spore formation over time, spore formation was determined to begin about 1 week after the introduction of hesperidin, the entire liquid surface of the medium was covered with spores after 3 weeks.

Samples of the culture liquid were collected from each flask at time thought to represent the intermediate and latter stages of spore formation, and more specifically, two weeks after the introduction of hesperidin but prior to complete termination of spore formation. The collected samples were separated by centrifugation (3000 rpm, 15 minutes) to precipitate impurities. The supernatant was analyzed by analytical high performance liquid chromatography (HPLC) followed by examination of the changes in flavonoid composition. The Model LC10A (produced by Shimadzu) was used for the HPLC system, while the ODS Column A303 (produced by YMC) was used for the column. As a result, the ratio of hesperidin conversion product relative to the entire flavonoid composition (peak area ratio) was about 8.3%.

The samples remaining after HPLC analysis that contained hesperidin conversion product were concentrated with an evaporator. The concentrated samples were fractionated by preparative HPLC (using the LC8A (produced by Shimadzu) for the HPLC system, and the ODS Column R353-151A, SH343-5 (produced by YMC) for the column) to isolate and purify the hesperidin conversion product.

<Determination of Structure>

The following provides an explanation of determination of the structure of the purified hesperidin conversion product.

The $^1$H-NMR, $^{13}$C-NMR and FAB-MS spectra of the hesperidin conversion product were measured. In the NMR measurement, tetramethylsilane (TMS) dissolved in DMSO-d6 was used for the internal standard. The Model JNM-EX-400 (produced by JEOL) (at 400 MHz for $^1$H-NMR and at 100 MHz for $^{13}$C-NMR) was used for the NMR system. The Model JMS-DX-705L (produced by JEOL) was used for the FAB-MS measurement system. The measurement results are shown in Tables 1 and 2. According to an analysis of the measurement results, the hesperidin conversion product was 8-hydroxyhesperetin having the structure represented by chemical formula 1.

TABLE 1

| $^1$H NMR(δ) | 11.73(1H, s, 5-OH) |
|---|---|
| | 10.39(1H, s, b, 8-OH) |
| | 9.03(1H, s, b, 3'-OH) |
| | 8.06(1H, s, b, 7-OH) |
| | 6.99(1H, d, J=.6Hz, H-2') |
| | 6.96(1H, d, J=8.4Hz, H-5') |
| | 6.93(1H, dd, J=8.4Hz, 1.6Hz, H-6') |
| | 5.94(1H, s, H-6) |
| | 5.43(1H, dd, J=11.8Hz, 3.2Hz, H-2) |
| | 3.80(s, OCH3) |
| | 3.17(1H, dd, J=17Hz, 11.6Hz, H-3ax) |
| | 2.76(1H, dd, J=17Hz, 3.2Hz, H-3eq) |
| FAB-MS(m/z) | 319[M + H]+ |

TABLE 2

| $^{13}$C NMR | |
|---|---|
| C | δ |
| 2 | 80.6 |
| 3 | 44.1 |
| 4 | 197.7 |
| 5 | 158.0 |
| 6 | 96.7 |
| 7 | 157.6 |
| 8 | 126.8 |
| 9 | 150.3 |
| 10 | 103.2 |
| 1' | 133.1 |
| 2' | 112.6 |
| 3' | 147.7 |
| 4' | 149.4 |
| 5' | 114.8 |
| 6' | 119.3 |
| Me | 56.5 |

<Measurement of Antioxidative Activity—1>

The antioxidative activity in a hydrophilic solvent was measured for hesperidin (HE) and the isolated 8-hydroxyhesperetin (8OH—HE). It should be noted that antioxidative activity was measured in accordance with the radical scavenging ability measurement method described in Yamaguchi, et al., Biosci. Biotechnol. Biochem., 62, 1201–1204, 1998.

More specifically, an 8OH—HE sample solution and HE sample solution were first prepared having concentrations of 0.1 μM, 1 μM and 10 μM by dissolving 8OH—HE or HE in ethanol. 200 μL of each sample solution was then mixed into 800 μL of 0.1 M Tris-HCl buffer (pH 7.4). 1 ml of 500 μM DPPH (1,1-diphenyl-2-picrylhydrazyl) in ethanol was added to each mixture to prepare reaction solutions. After adequately mixing the reaction solutions, they were allowed to react for 20 minutes in a dark location at room temperature.

Next, 20 μL of each reaction solution was injected into an analytical HPLC system (LC-10A) using a microsyringe to analyze the DPPH concentration. The DPPH concentration was calculated from peak area of DPPH. It should be noted that a column having an inner diameter of 4.6 mm and length of 150 mm (TSKgel Octyl-80TS, produced by YMC) was used in HPLC analysis, the elution solvent consisted of a 30:70 ratio of distilled water and methanol, the flow rate was 1 mL/minute and the detection wavelength was 517 nm.

Using 200 μL of a solution of ethanol only instead of the sample solutions for the control, the peak area of DPPH was similarly measured for the control by HPLC analysis. The radical scavenging activity (%) of 8OH—HE and HE were then determined according to the calculation formula indicated in Formula 1.

$$\text{Radical scavenging activity} = 100 - \frac{\text{DPPH peak area of sample}}{\text{DPPH peak area of control}} \times 100 \quad \text{(Formula 1)}$$

Furthermore, the higher value for radical scavenging activity, the higher the antioxidative activity. The results are shown in FIG. 1. The 8OH—HE formed from HE by fermentation treatment was determined to demonstrate a much higher level of antioxidative activity than HE in the hydrophilic solvent.

<Measurement of Antioxidative Activity—2>

The antioxidative activity in a hydrophobic solvent was measured for hesperidin (HE), isolated 8-hydroxyhesperetin (8OH—HE) and α-tocopherol (Toc), a compound that is known to have a high level of antioxidative activity. Incidentally, antioxidative activity was measured by HPLC analysis using methyl linoleate as described in Terao J., et al., Lipids, 21(4), 255–260, 1986.

More specifically, an 8OH—HE sample solution, HE sample solution and Toc sample solution having concentrations of 100 μM were first prepared by dissolving 8OH—HE, HE and Toc in ethanol. 89 mg (100 μL) aliquots of methyl linoleate were each weighed into three small test tubes having an inner diameter of 14 mm. 100 μL of each sample solution was added to the three test tubes and mixed well to prepare mixtures.

Next, each of the mixtures was dried by completely removing the solvent by placing each test tube in a vacuum desiccator in which pressure was reduced using a vacuum pump. Each test tube was allowed to stand undisturbed in a dark location at 40° C. for 18 hours. Subsequently, 0.08% BHT (butyl hydroxyl toluene) was added to each test tube. The sum of the HPLC peak areas of 13-hydroperoxide and 9-hydroperoxide formed by the methyl linoleate was then determined.

Moreover, HPLC analysis was also performed using 100 μL of a solution of ethanol only instead of the sample solutions for the control. The sum of the HPLC peak areas of the control was also determined. The degree of lipid peroxidation (%) of each sample was then determined from Formula 2. The lower the level of lipid peroxidation, the higher the antioxidative activity. The results are shown in FIG. 2.

$$\text{Degree of lipid peroxidation} = \frac{\text{Sample peak area}}{\text{Control total peak area}} \times 100 \quad \text{(Formula 2)}$$

Figure 2:
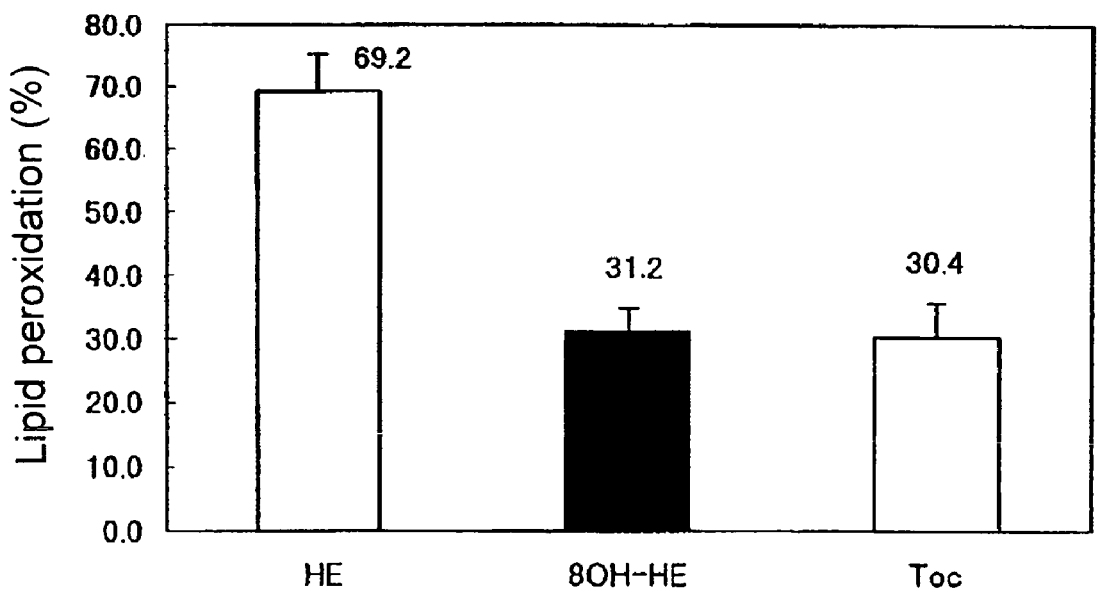

According to the results of FIG. 2, the 8OH—HE formed from HE by fermentation treatment demonstrated a much higher level of antioxidative activity than HE in the hydrophobic solvent, and also was determined to demonstrate antioxidative activity that was comparable to α-tocopherol.

INDUSTRIAL APPLICABILITY

According to the present invention, a flavonoid compound that has a comparatively high antioxidative activity in both hydrophilic and hydrophobic solutions and its preparation process are provided. According to this process, a novel flavonoid compound that is more efficiently absorbed into the body than hesperidin is produced from hesperidin. Since compositions that contain this flavonoid compound demonstrate antioxidative activity, they can be used in, for example, nutritional foods, thereby expanding the range of use of hesperidin.

What is claimed is:

1. A flavonoid compound having a structure represented by the following chemical formula 1

(Chemical Formula 1)

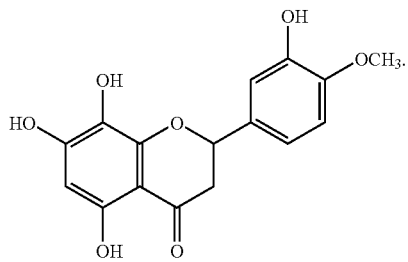

2. The flavonoid compound according to claim 1 characterized in that it has an antioxidative activity.

3. The flavonoid compound according to claim 1 characterized in that it is obtained by microbial fermentation of hesperidin by *Aspergillus saitoi*.

4. A composition containing an antioxidative flavonoid compound having the structure represented by the following chemical formula 1

(Chemical Formula 1)

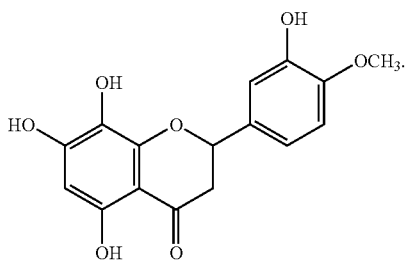

5. The compound according to claim 1, said compound synthesized by microbial conversion.

6. The compound according to claim 5, wherein the compound is isolated from culture medium.

7. The composition according to claim 4, said compound synthesized by microbial conversion.

8. The composition according to claim 7, wherein the compound is isolated from culture medium.

* * * * *

UNITED STATES PATENT AND TRADEMARK OFFICE
CERTIFICATE OF CORRECTION

PATENT NO.         : 7,138,429 B2                              Page 1 of 1
APPLICATION NO. : 10/471438
DATED              : November 21, 2006
INVENTOR(S)        : Toshihiko Osawa et al.

It is certified that error appears in the above-identified patent and that said Letters Patent is hereby corrected as shown below:

On Title Page

Item (73) on the first page of the issued patent is changed to recite the full, unabbreviated legal names of each of the three assignees of record.

should read

(73) Assignee: Japan Science and Technology Corporation, Saitama (JP); Japan as Represented By President of Nagoya Univeristy, Aichl (JP); and Pokka Corporation, Aichi (JP)

Signed and Sealed this

Eleventh Day of September, 2007

JON W. DUDAS
*Director of the United States Patent and Trademark Office*